(12) United States Patent
Dixon et al.

(10) Patent No.: US 6,666,870 B2
(45) Date of Patent: Dec. 23, 2003

(54) METHOD UTILIZING CHEMICAL BONDING TO IMPROVE THE BONE SCREW FIXATION INTERFACE

(76) Inventors: Robert A Dixon, 10577 Durham Pl., Powell, OH (US) 43065; Donald J. Hackman, 3499 Kirkham Rd., Columbus, OH (US) 43221

(*) Notice: Subject to any disclaimer, the term of this patent is extended or adjusted under 35 U.S.C. 154(b) by 22 days.

(21) Appl. No.: 10/034,815

(22) Filed: Dec. 27, 2001

(65) Prior Publication Data

US 2002/0095158 A1 Jul. 18, 2002

Related U.S. Application Data

(60) Provisional application No. 60/259,917, filed on Jan. 5, 2001.

(51) Int. Cl.[7] .............................................. A61B 17/56
(52) U.S. Cl. ............................ 606/76; 606/69; 606/73
(58) Field of Search ............................ 606/61, 69, 71, 606/79, 76, 72, 73; 411/82, 82.1, 304, 417, 418

(56) References Cited

U.S. PATENT DOCUMENTS

| | | | |
|---|---|---|---|
| 4,655,203 A | | 4/1987 | Tormala et al. |
| 4,657,460 A | * | 4/1987 | Bien ........................... 411/258 |
| 4,987,714 A | * | 1/1991 | Lemke ......................... 52/410 |
| 5,550,172 A | | 8/1996 | Regula |
| 5,569,250 A | * | 10/1996 | Sarver et al. ................. 606/69 |
| 5,837,752 A | * | 11/1998 | Shastri et al. ................ 523/116 |
| 5,941,911 A | * | 8/1999 | Buechel ..................... 623/11.11 |
| 6,206,881 B1 | * | 3/2001 | Frigg et al. .................... 606/69 |
| 6,228,085 B1 | * | 5/2001 | Theken et al. ................. 606/61 |
| 6,241,771 B1 | | 6/2001 | Gresser et al. |
| 6,316,523 B1 | | 11/2001 | Hyon et al. |
| 6,325,804 B1 | | 12/2001 | Wenstrom, Jr. et al. |
| 6,342,055 B1 | * | 1/2002 | Eisermann et al. ............ 606/69 |
| 6,527,553 B2 | * | 3/2003 | Yeung ......................... 433/173 |

OTHER PUBLICATIONS

Patrick J. Courtney and Christopher Verosky Advances in Cyanoacrylates Technology for Device Assembly.
Medical Device & Diagnostic Industry Magazine Sep. 1999, pp. 1, 4, 5, 7, 9 of 14.
Canon Communications.

* cited by examiner

*Primary Examiner*—Pedro Philogene
*Assistant Examiner*—David A Bonderer

(57) ABSTRACT

This invention relates to a method and materials in combination for bonding screws to a fixation plate or to a skeletal bone using chemical means. The chemicals include solvents, glues, or bonding agents, which act to improve the strength of bone screw to plate or the bone screw to skeletal bone interface. Interface refers to the contact area between the bone screw and either the plate or skeletal bone. The fixation device usually comprises a plate with bone screws implanted within the human skeleton. The bone screw maintains the plate in contact with the bone or maintains another structure such as a tendon in contact with the bony skeleton. The chemical bonding is in addition to or in place of a mechanical means to bond the bone screw to the fixation plate or to the skeletal bone. It provides for added strength to the bone screw interface with a plate or skeletal bone, reducing the probability of screw loosening and or migration.

9 Claims, 3 Drawing Sheets

| Ethyl 2-Cyanoacrylate | | | | | |
|---|---|---|---|---|---|
| Viscosity | Viscosity cps. | Consistency comparison | Gap filling | Cure time seconds | filler |
| Thin | 5 | Water | .1mm/.004" | 5 – 6 | None |
| Medium | 100 | Glycerin | .5mm/.010" | 6 – 10 | Silica Sio2 |
| Medium thick | 1000 | Syrup | 1mm/.020" | 10 – 25 | Silica Sio2 |
| Thick | 2000 | Honey | 2mm /.040" | 50 – 60 | Silica Sio2 |

FIG.7

METHOD UTILIZING CHEMICAL BONDING TO IMPROVE THE BONE SCREW FIXATION INTERFACE

CROSS-REFERENCES TO RELATED APPLICATIONS:

This patent application was preceded by:
Provisional Patent No. 60/259,917 with a file date of Jan. 5, 2001.

STATEMENT REGARDING FEDERALLY SPONSORED RESEARCH OR DEVELOPMENT

Not applicable

REFERENCE TO A MICROFICHE APPENDIX

Not applicable

BACKGROUND OF THE INVENTION

This invention relates generally to internal fixation means to be adapted to be implanted within the body in direct contact with a bone or bone fragment for the purpose of reinforcement of said bone or bone fragments relative to one another. It relates more specifically to implantable medical devices wherein the internal fixation means is adapted for positioning vertebrae.

In normal anatomy, the human skeleton is supported by a complex arrangement of ligaments, tendons, joints, and muscles. Congenital disorders, degenerative diseases, malignancies, medical conditions or trauma may cause abnormal conditions. These problems generally cause or allow abnormal displacement or rotation of bones, tendons, or joints. These conditions may require surgical alteration of the existing anatomy.

Fixation of surgical changes is frequently necessary during the healing process because failure to maintain proper alignment between the healing tissues will result in a less than optimal outcome or complete failure of the surgical procedure. Screws and other devices such as plates, hold the bones and tendons in the desired anatomic alignment until healing occurs or the fixation device fails. Loosening of the bone screw from the skeletal bone or from the fixation device is a major contributor to fixation failure. Screw back out and loosening has led to the development of mechanisms for locking the screws in metal plates. These locking mechanism contain intricate components that increase the cost and reduce reliability.

Once healing takes place these fixation devices are no longer needed and may cause complications. If healing does not occur, all fixations with screws and or plates will eventually fail or break.

Improvement of the bone to screw interface is the driving force behind multiple patents and ongoing research for mechanical locks. Bonding is one of the advances toward improving bone to screw interfaces and reducing surgical failure. Simpler more reliable metallic bone fixation systems and methods for the use of polymeric fixation systems are needed. The process and materials of the present patent will improve these fixation systems.

BRIEF SUMMARY OF THE INVENTION

Internal fixation is a temporary means to hold the bones in the proper alignment while the body heals the area with living tissue. Polymers, including bio-absorbable and bio-degradable materials will allow the temporary fixation devices to be reabsorbed or incorporated into the patient's anatomy after healing takes place. These polymers require fixation methods, which will not create stress concentrations in the low strength polymeric screws and plates holding the implants. The present patent provides chemical means, through the use of solvents, glues, or bonding agents, for improving the bone screw interface in polymeric materials without creating stress concentrations.

BRIEF DESCRIPTION OF THE SEVERAL VIEWS OF THE DRAWING

FIG. 7 is a table of Ethyl 2-Cyanoacrylate properties.

DETAILED DESCRIPTION OF THE INVENTION

Figure 3:
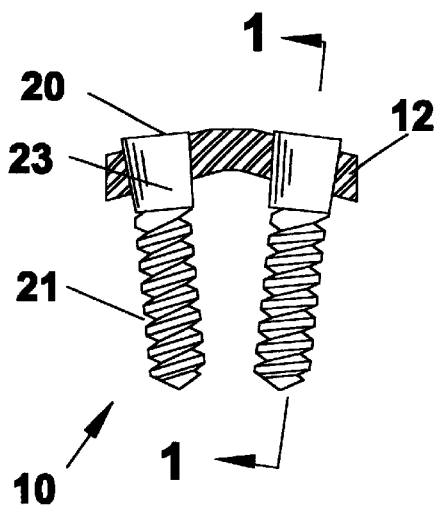
FIG. 3 is a top sectional view, at 3—3, of FIG. 1, of a spinal stabilization system shown with the vertebrae removed.

This process comprises the implantation of a plate 12 and bone screws 20 fabricated from metals, alloys, non-metals, polymers, plastics, or biologic materials used in conjunction with adhesives or composite materials. There are three interfaces, shown in FIGS. 1 and 3: The bone screw to plate interface (herein referred as the screw-plate interface), the bone screw to skeletal bone (hereafter referred as the bone screw-skeletal interface), and the plate to bone surface (hereafter referred as the plate-skeletal interface). Interface refers to the contact area or gaps between the bone screw and either the plate or skeletal bone.

The said screw is attached to a fixation plate 12 or skeletal bones 31 and 32, using chemical bonding means. For simplification the screw-plate interface, screw-skeletal interface, and bone-plate interfaces are presented in one of many conceivable embodiments. The bonded interfaces act to improve device strength and seal the interfaces from wear and loosening. That is not to imply that this is the only embodiment or material selection method within which the bone screw-plate bonding can be performed. There are three interfaces that may be improved with bonding materials.

The Screw to Bone Interface

Figure 1:
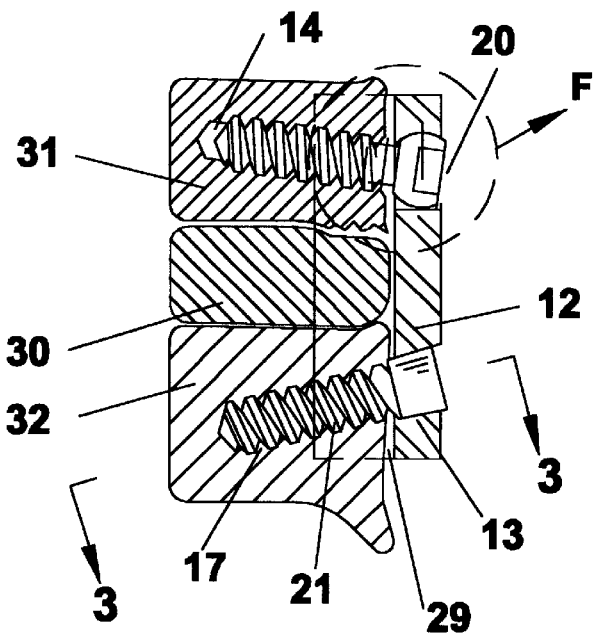
FIG. 1 is a side sectional view, at 1—1 of FIG. 3, of a typical stabilization system, which will be improved, with the use of chemical bonding. It is shown implanted on the cervical portion of a human spinal column with a spherical head screw on the upper and a tapered head screw on the lower vertebra.

In the preferred embodiment, as shown in FIG. 1, a bone screw 20 is threadibly engaged in the vertebral bone 31 or 32, to hold the plate 12 rigidly to the vertebra. The screw thread 17 in the bone is the most likely material to shear out during implantation and postoperative. The bone thread 17 may be drilled and tapped, predrilled and formed with self-tapping screws, or the screw may be self-drilling and self-tapping. These attachment techniques are well known to those practiced in the art.

While preparing the threaded bone screw holes 14 and 17, the surgeon can determine if there are porous or soft spots in the bone thread 17 of the screw. These spots may require reinforcement with a filler/bonding material. One of weakest points of the screw is the stress riser where the thread runout leaves a groove in the screw shank 26, shown in FIGS. 5 and 6, near the screw head 23. If the screw is rigidly fixed in the bone, the predominate stresses are uniform shear, however if the screw is loose it can create bending stresses at the point of the least cross section. Loose threads in the bone and the low compression modulus of the bone material allow the screw to move relative to the bone 31 and the plate 12. Since screw bending is primarily caused by a loose fitting screw, bonding the screw to the bone can add strength to the implant while healing occurs.

The Screw to Plate Interface

Figure 2:
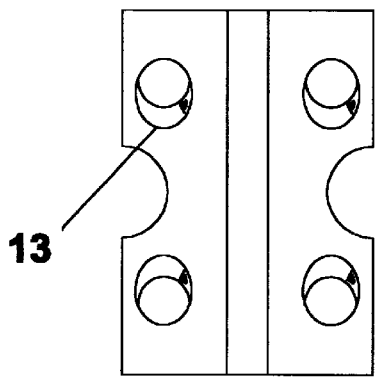
FIG. 2 is a front (proximal) view of the said plate.

The plate 12 is the framework upon which the bone screws 20 are attached. The plate 12 has two holes 13, shown in FIGS. 1 and 2, per vertebrae, on a centerline perpendicular to the patient's spinal axis to receive and contain the bone screws 20. In the preferred embodiment the plate 12 is fabricated from a single piece of material, preferably a nonmetal polymer. In prior art these plates contained locking threads for locking the screw or small locking devices such as cams to prevent the bone screws from backing out under sustained or repetitive movement of the patient. Some materials do not have the yield, tensile, compressive, endurance, or shear strengths required to maintain the clamping force of the small area of locking threads within the plate. This makes the locking thread prone to being easily stripped during installation of the screw lock or loosening during normal daily activities of the patient after implantation. Locking mechanisms can be expensive to place on or within the plate.

Figure 4:
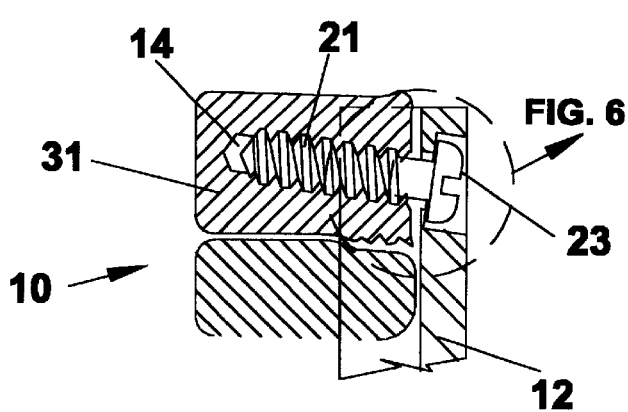
FIG. 4 is a side sectional view, of 1—1 of FIG. 3, of a plate attached using a button head screw, showing the locations in which the chemical bonding may be used.
Figure 5:
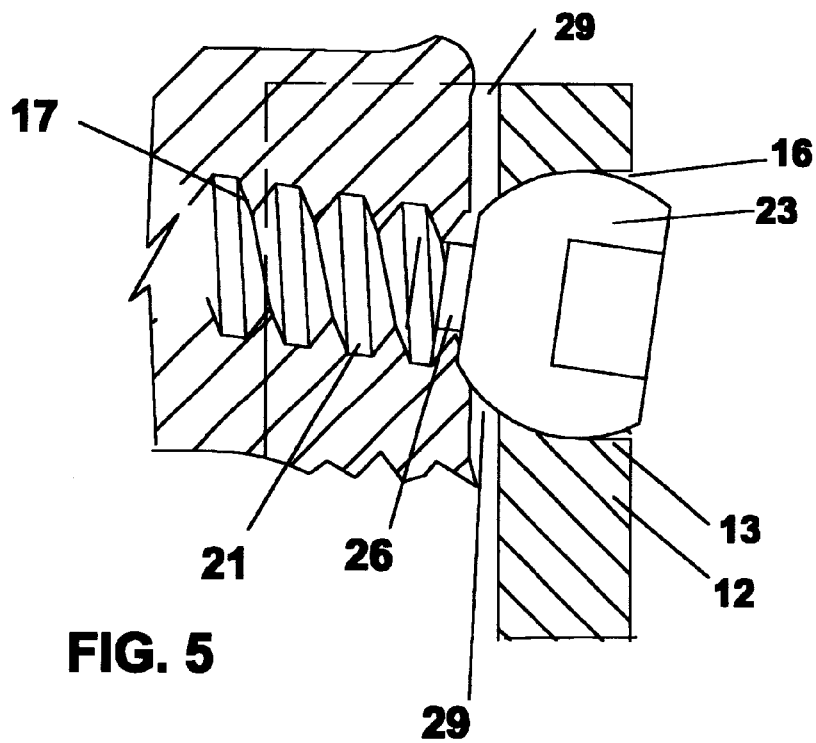
FIG. 5 is an enlarged view of the circled area of FIG. 1, showing the spherical head screw and the locations where the chemical bonds may be used.
Figure 6:
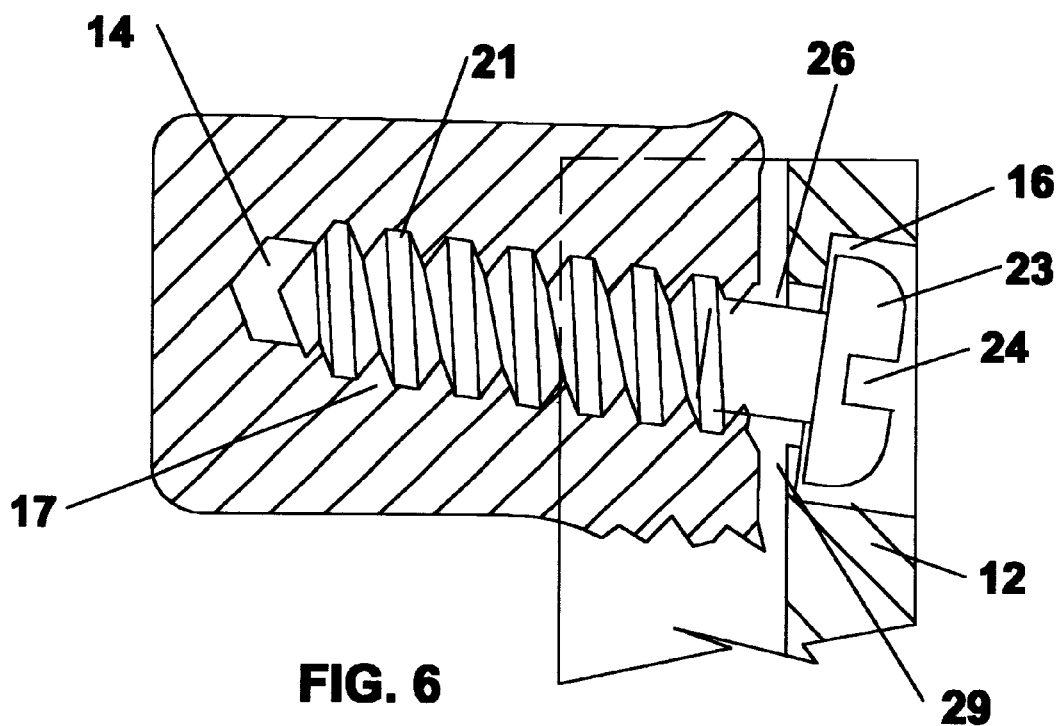
FIG. 6 is an enlarged view of the button head screw of the circled area of FIG. 4 and the locations where the chemical bonds may be used.

To eliminate the use of plate threads or other complicated locking mechanisms on these plates, the screw 20 is held in place by bonding the screw-plate interface 16 in FIGS. 4, 5, and 6. Placement of the plate 12 and positioning the screws 20 is well known to those practiced in the art. Bonding can be completed by the use of adhesives or solvents, forming bonds between the adjacent components. In the preferred embodiment cyanoacrylate compound is used to bond a polymeric non-metallic screw 20 to a polymeric non-metallic plate 12. A supplementary locking mechanism can also be used. Some of these are under development and others are well known to those practiced in the art. The method of stabilizing the area and maintaining the relationship between the two vertebras is still a changing technology. Bonding the screw prevents backout and rigidizes the construct to support the plated area during the healing process as outlined above.

The Plate to Bone Interface

The plate 12 is the component that provides the fixation upon which the bone screws 20 are attached. Maintaining the plate tight to the vertebra increases the rigidity of the graft 30. The plate surface is usually relatively smooth compared to the vertebra interface, so the contact area is small. Filling the depressions with gap filler adhesive may increase this contact 29, shown in FIGS. 5 and 6.

Description of the Method of Implanting

Accelerators or primers may be applied to the substrates being bonded prior to adhesive application in order to minimize setup time and improve bonding. Generally, the accelerator (or primer) is applied to one surface while the adhesive is applied to the mating surface. This accelerator prevents the adhesive from curing before the parts can be mated. Accelerators can also be sprayed over cyanoacrylates to cure fillets of adhesive or unconfined drops. Accelerators (and primers) may be used for the following actions: control the cure time from 10 seconds to 180 seconds; control the depth of penetration of porosity; control the curing thickness from 0.010 to 0.1 inches depth; clean the surface; provide different cure time on selected zones of the component by coating each with different accelerators; and bond dissimilar materials.

The bonding steps are dependent upon the following criteria: bone density, porosity, hardness, and the surface of the plate-bone interface. The steps for bonding include trial assembly, prealignment, application, and temporary fixation. If a thin gap exists between the mating substrates (for example a screw-plate interface), the cyanoacrylate can wick into the area. The more porous the material, the heavier the coat of cyanoacrylate needed.

There are 3 zones in which adhesives may be used to increase the rigidity of the system. The zones are shown in FIG. 6. (1) The threaded portion of the fastener 21. (2) The fastener shank 26 from the thread area to the head, and (3) The head 23 of the fastener 20. The preparation and the bonding begins after the hole is threaded 17.

Preparation of the mating surfaces may include the following:

1. Determine if the bone has soft or porous sections in the threaded portion 17.
2. If there is porosity, inject adhesive in the hole 14.
3. Spray primer on the screw threads 21 and 17.
4. Inject the adhesive around the hole 14 in the bone.
5. Spray a quick set primer on the portion of the screw head 23 that contacts the plate 12.
6. Inject or coat the adhesive in and around the plate hole 13.
7. Place the plate 12 on the vertebra.
8. Insert the screw until the screw threads engage the bone internal thread 17.
9. Tighten the screw 20 with a driver in slot 24.
10. Inject the adhesive around the screw-plate gap space 16 to allow for wicking.
11. Spray accelerator/primer over the gap 16.

Description of the Materials

The types of adhesives commonly used for medical device assembly include cyanoacrylates, light-curable acrylics, light-curable cyanoacrylates, epoxies, urethanes, and dual UV/moisture-curable silicones. In general, adhesives offer several benefits compared with other assembly methods. These include the ability to fill large gaps, to bond dissimilar materials, to distribute stress evenly across a bond line, and to form a seal when confined between two substrates.

There are many bonding materials available however, to date the only adhesives which have the properties necessary for implants are the cyanoacrylates. Some of the advantages of cyanoacrylate adhesives include: simple to apply, fast setup and cure, non toxic, biocompatible, require little pre-operative preparation, are long lasting, and moisture tolerant.

Cyanoacrylate adhesives provide benefits that make them well suited for use in medical applications. The cyanoacrylates have a wide variety of formulations offering performance and process variations. Some of these products include surface-insensitive cyanoacrylates. These cure well on acidic surfaces. Another variation includes rubber-toughened cyanoacrylates, which have improved peel strength. A standard ethyl cyanoacrylate tested in peel provides an average strength of less than 3 lb. per width inch. In comparison, a rubber-modified cyanoacrylate exhibits peel strengths of approximately 40 lb. per width inch. There are thermal resistant cyanoacrylates, which provide long-term performance. The liquid characteristics of typical materials are shown in FIG. 7.

Cyanoacrylate adhesives are cyanoacrylate esters, of which methyl and ethyl cyanoacrylates are the most commonly used in adhesive formulation. They are stabilized and stored through the addition of a weak acid. After application they polymerize in the presence of a weak base such as water. When the adhesive contacts a surface, trace amounts of water or other basic material present on the surface neutralize the acidic stabilizer in the adhesive, resulting in the rapid polymerization of the cyanoacrylate. Once cured, cyanoacrylates form thermoplastic polycyanoacrylate, which is a stable, inert material at room temperature.

Methyl cyanoacrylates are based on the methyl cyanoacrylate monomer. This monomer has the lowest molecular weight of any cyanoacrylate monomer, and consequently leads to the most rigid polymer matrix. While generally superior to ethyl cyanoacrylates for metal-bonding applications, they do not offer the durability of rubber-toughened products on metal surfaces.

Ethyl cyanoacrylates are based on the ethyl cyanoacrylate monomer, the most commonly used monomer in cyanoacrylate adhesives. In general, ethyl cyanoacrylates give better performance on plastics and elastomeric substrates compared with methyl cyanoacrylates.

Viscosity

In the adhesive's uncured state, the viscosity of the cyanoacrylates ranges from water-thin liquids to gels. Low-viscosity products, also known as wicking-grade adhesives, can be applied to components that have been fitted together. The cyanoacrylate will rapidly fill the bond area through capillary action. High viscosity fluids use thickeners such as polymethylmethacrylate resin and silica. While the wicking-grade-viscosity products will tend to run out of any gap larger than 0.001–0.002 in., the higher-viscosity products can be used on much larger gaps. The gels can even be applied to inverted or vertical surfaces and will not drip or run. It is still best to keep joint gaps no larger than 0.010 in., even though these products can be used in still-larger gaps without flowing. The limiting factor in joint-gap design for the higher-viscosity products is the ability of the adhesive to cure through the entire gap.

Primers and Additives

The cyanoacrylate curing process is surface initiated, and consequently it is difficult to achieve complete cure when a large volume of the adhesive is not in close proximity to a surface. If the relative humidity falls below 30%, the cure rate will drop dramatically. It is best to use a surface-insensitive product in this situation or an accelerator if the humidity cannot be maintained at an acceptable level.

On acidic surfaces, or in low-humidity environments, the neutralization of the acidic stabilizer may be hindered, leading to long setup times. Surface-insensitive cyanoacrylates are formulated by adding agents such as silicones and ethers to ethyl cyanoacrylates by minimizing the effects of surface acidity and dryness. These products generally offer the most rapid setup times of all cyanoacrylates.

The capabilities of cyanoacrylate adhesives can be expanded through the use of specialty accelerators and primers. Cyanoacrylate accelerators are made up of a basic material dispersed in a solvent such as acetone or isopropyl alcohol. Accelerators can be applied to the substrates being bonded prior to adhesive application in order to minimize setup time. Generally, the accelerator is applied to one surface while the adhesive is applied to the mating surface, this prevents curing of the adhesive by the accelerator before the parts can be mated. Accelerators can also be sprayed over cyanoacrylates to cure fillets of adhesive or unconfined drops.

The solvent-based primers allow for significant increases in bond strength of many materials that are normally difficult to bond, including polyethylene, polypropylene, fluoropolymer, and acetyl homopolymer. They are also room-temperature-curable and available in a wide range of viscosities. Cyanoacrylates cure rapidly to form rigid thermoplastics with excellent adhesion to most substrates. They typically setup within 1 minute and achieve full bond strength in 24 hours.

Moisture Resistance

Tests have shown that the materials being bonded effect the resistance of a cyanoacrylate-bonded joint to long-term exposure to humidity or immersion in water. On metals such as aluminum and steel, exposure to humidity leads to a decrease in bond strength for all types of cyanoacrylates. On polymeric materials such as ABS and polycarbonate, however, even standard ethyl cyanoacrylates showed good bond-strength retention after 4 weeks of immersion in water.

DERMABOND® is an Ethyl Cyanoacrylate adhesive that cures in the presence of moisture. As it is applied to a surface, the moisture on the surface initiates the bonding process and begins to form bonds with the surfaces being glued. It is intended for topical application to close skin edges of wounds from surgical incisions, from minimally invasive surgery, and from trauma-induced lacerations. The adhesive is a sterile, liquid adhesive containing a monomeric (2-octyl cyanoacrylate), which is compatible with gamma and EtO sterilization methods. As it is applied, the adhesive reacts with moisture on the skin's surface to form a strong, flexible bond in 45 to 60 seconds and reaches its full strength in approximately two and a half minutes. As the wound heals, the adhesive sloughs (wears away) from the skin, and complete healing usually occurs in five to ten days. Octyl-cyanoacrylate (Dermabond®) is approved by the Food and Drug Administration for laceration closure.

®Trademark of Ethicon, Inc

Other Adhesives

Light-curable cyanoacrylates are ethyl-based products. their overall physical-performance characteristics are similar to those obtained with traditional cyanoacrylates. benefits include minimal blooming (since exposed, uncured cyanoacrylate can be immediately cured using ultraviolet and/or visible light), increased depth of cure compared with the traditional maximum cyanoacrylate cure depth of 0.010 in., and compatibility with primers for hard-to-bond plastics, however they cannot be used with buried or translucent components. Light-curable acrylic adhesives undergo a free-radical reaction to form thermoset resins. Like cyanoacrylates, light-curable acrylics range from low-viscosity formulations to gels. The critical processing key with light-curable acrylics is that light must reach the full bond line in order to cure the adhesive; any adhesive in shadowed areas will not cure. In addition, the maximum depth of cure for the majority of light-curable acrylic systems is approximately 1 mm (0.04 in).

Epoxy adhesives cure to form thermoset plastics with a polymerization reaction by catalysts. Both room temperature and heat curable one- and two-part systems are available. Because of their ability to cross-link, epoxies offer superior chemical, environmental, and thermal resistance. Since epoxies cure via an exothermic reaction (giving off heat during cure), they can cure in thick sections.

Polyurethane adhesives, like epoxies, come in one- and two-part formulations. A urethane linkage occurs when the two main components are polyol and an isocyanate are mixed. A drawback to the use of polyurethanes is their inherent sensitivity to moisture. Excess moisture on a part or in one of the adhesive components can cause a reaction that results in the evolution of carbon dioxide and the presence of bubbles in the finished configuration.

Silicones form flexible polymers when cured exhibit low cohesive strengths, the ability of the polymer to adhere to itself. Although two-part industrial silicone systems do exist, the catalysts used in such materials typically cause them to fail biocompatibility screening.

We claim:

1. A process for fixing, stabilizing, or rigidizing individual bone segments in a bone column, said process comprising the steps of:
   (a) providing at least one plate formed to be positioned relative to bone segments for engagement therewith,
   (b) providing a plurality of fasteners for engagement with a plurality of holes in the at least one plate, and for engagement to the bone segments, applying a chemical bonding agent applied at the time of securing said fasteners with said at least one plate; wherein
       said bonding agent is applied to selected portions of the fasteners and the at least one plate wherein the fasteners and the plate are secured to one another.

2. The process of claim 1, wherein the bonding agent is a cyanoacrylate.

3. The process of claim 1, wherein the bonding agent is applied to bond the fastener to the plate at a surface interface where the fastener and plate are engaged.

4. The process of claim 3, wherein the bonding agent is applied after the fastener is secured in engagement with the plate, allowing the bonding agent to wick into the interface where the fastener and the plate are engaged.

5. The process of claim 1, wherein the bonding agent is applied to bond the fastener to the bone segment at an interface where the fastener and the bone are engaged.

6. The process of claim 1, wherein the bonding agent is applied to an interface where the bone segment and the plate are engaged.

7. The process of claim 1, wherein the fastener is a screw.

8. A process for retaining a plurality of fasteners and at least one plate for fixing, stabilizing, or rigidizing individual bone segments in a bone column, said process comprising the steps of:
   (a) applying a chemical bonding agent at the time of securing a fastener with said at least one plate, and applying said bonding agent to selected portions of the fasteners and the at least one plate wherein the fasteners and the plate are secured to one another and to the bone segments; and
   wherein the bonding agent strengthens and seals a fastener to plate interface, a fastener to bone segment interface, and a plate to bone segment interface, wherein an interface is defined as a contact area between the fastener and the plate, the fastener and the bone segment, and the plate and the bone segment.

9. A method of retaining a plurality of fasteners, wherein each fastener has a head, a shank, and a threaded portion, and at least one plate having a plurality of holes to individual bone segments in a bone column comprising the steps of:
   providing a cyanoacrylate bonding agent;
   providing a cure time control primer, wherein the primer accelerates setup time and improves bonding of the bonding agent;
   determining porosity of the bone segment;
   injecting the bonding agent into a porous section of the bone segment;
   coating the primer onto the threaded portion of the fastener;
   positioning the plate on the bone column;
   inserting and partially threading the fastener through at least one pre-drilled hole of the plate, wherein a gap between the fastener and the plate is formed and the threaded portion of the fastener engages the bone segment;
   injecting the bonding agent into the gap between the fastener and the plate; and
   tightening the fastener until the fastener head engages the plate.

* * * * *